US005282462A

United States Patent [19]

Kudo

[11] Patent Number: 5,282,462

[45] Date of Patent: Feb. 1, 1994

[54] MOUTHPIECE FOR REGULATOR

[76] Inventor: Masao Kudo, II-I0, Ehara-cho I-chome, Nakano-ku, Tokyo I65, Japan

[21] Appl. No.: 964,183

[22] Filed: Oct. 21, 1992

[30] Foreign Application Priority Data

Oct. 30, 1991 [JP] Japan ............................ 3-097377[U]

[51] Int. Cl.[5] ............................................ A61M 16/00

[52] U.S. Cl. ........................... 128/204.26; 128/206.29

[58] Field of Search ...................... 128/204.18, 204.26, 128/201.11, 206.29

[56] References Cited

U.S. PATENT DOCUMENTS 1,210,939 1/1917 Hilgers .......................... 128/201.11
4,031,888 6/1977 Walters .......................... 128/201.11
4,230,106 10/1980 Geeslin et al. ................ 128/201.11
4,862,903 9/1989 Campbell ....................... 128/201.11
5,031,611 7/1991 Moles ............................ 128/201.11
5,048,519 9/1991 Kasama et al. ................ 128/201.11

*Primary Examiner*—Edgar S. Burr
*Assistant Examiner*—Aaron J. Lewis
*Attorney, Agent, or Firm*—Jordan and Hamburg

[57] ABSTRACT

A mouthpiece for a regulator is of a structure in which it is possible to freely utter words, and to talk even when a driver wears the regulator. The mouthpiece 10 is mounted under a communicating condition on a demand regulator unit 2 which is connected to a cylinder through a hose 4. The mouthpiece 10 comprises a tube 12 abutted against an outer side of a mouth portion of a diver, and a pair of teeth grips 13 extending from the tube into a cavum oris of the diver, so as to be bitten and held by molar teeth of the diver. When the mouthpiece 10 is worn, the mouth portion of the diver is made free. Accordingly, talking and conversation are made possible while being worn.

5 Claims, 5 Drawing Sheets

MOUTHPIECE FOR REGULATOR

BACKGROUND OF THE INVENTION

1. Field of the Invention

The present invention relates to a regulator used to execute breathing at diving and, more particularly, to a mouthpiece which is worn to a regulator, capable of uttering words.

2. Related Art And Prior Art Statement

FIG. 6 of the attached drawings shows a regulator which has conventionally been used. The regulator 50 is provided with a demand regulator unit 51 to which a hose 52 is connected, and a mouthpiece 53 and an exhaust tube 54 arranged on the wearing side of the demand regulator unit 51. The demand regulator unit 51 is connected to a bomb or cylinder (not shown) through the hose 52, to execute pressure-reduction regulation of high pressure air supplied from the cylinder. The mouthpiece 53 supplies the air from the demand regulator unit 51, into a cavum oris of a diver. The mouthpiece 53 is provided with a skirt 55 inserted into a mouth portion of the cavum oris of the diver, and a pair of teeth grips 56 provided on both sides of the skirt 55 in a longitudinal direction. The mouthpiece 53 is made of a soft material such as plastics, rubber or the like, as a whole.

FIGS. 7 and 8 show a using condition of the regulator 50. A diver A takes the skirt 55 of the mouthpiece 53 in the mouth portion (a portion between teeth and lips) of the cavum oris, whereby the skirt 55 is elastically bent within the cavum oris B. Further, the teeth grips 56 are bitten and held by foreteeth of the diver A, whereby the demand regulator unit 51 is worn to the mouth portion of the diver A. At this wearing, the exhaust tube 54 functions to lead air exhausted from the cavum oris of the diver A, to the outside.

In this manner, the conventional regulator is worn such that the entire mouthpiece 53 is inserted into the mouth portion of the cavum oris of the diver A, and the teeth grips 56 are bitten and held by the foreteeth. Accordingly, opening and closing operation of a mouth is restricted at wearing. For this reason, when the mouthpiece 53 is worn, it is inconvenient, words cannot be uttered and talking is impossible. Thus, the pleasure of underwater swimming of the diver is reduced in half.

OBJECTS OF THE INVENTION

It is an object of the invention to provide a mouthpiece for a regulator, which can dissolve the above-discussed disadvantages and problems, and which is so enlarged in degree of freedom as to be capable of uttering words and talking, as compared with a conventional regulator.

It is another object of the invention to provide a mouthpiece for a regulator, which is simple in structure, is simple in using method, and is capable of sufficiently enjoying the pleasure of underwater swimming of a diver.

SUMMARY OF THE INVENTION

According to the invention, there is provided a mouthpiece of a regulator, which is mounted on a demand regulator unit connected to a bomb or cylinder through a hose, to supply air from the cylinder to a cavum oris of a diver, in which the mouthpiece is provided with a tube so worn as to be abutted against an outer side of the cavum oris of the diver under such a condition as to be in communication with the demand regulator unit, and a pair of teeth grips extending from the tube toward molar teeth in the cavum oris of the diver and bitten and held by the molar teeth, whereby the teeth grips are bitten and held by the molar teeth of the diver, so that the mouthpiece is worn, and breathing through the demand regulator unit is made possible. Upon wearing of the mouthpiece of the regulator, the tube is abutted against the outer side of the mouth of the diver, and the teeth grips are bitten and held by the molar teeth. Accordingly, opening and closing of the mouth are made free, and talking under the worn condition is made possible.

Moreover, an exhaust tube for emitting air exhausted from the mouthpiece to the outside is mounted on the demand regulator unit so as to be located below the mouthpiece. The mouthpiece is provided with a connection in which an attaching tube of the demand regulator unit is fitted detachably, and the tube connected integrally to the connection such that an interior of the tube is in communication with the connection, the tube having a side thereof adjacent to an open end thereof, which is substantially in the form of a horizontally elliptic configuration correspondingly to a mouth portion of the diver. The mouthpiece is made of a soft elastic material such as plastic, rubber or the like as a whole. Further, the teeth grips are integrally provided with connecting rods, respectively, which are inserted into the tube of the mouthpiece. Inserting ends of the respective connecting rods are coupled to the tube so as to be integrated with the tube. The teeth grips are integrally provided with laminate biting portions, respectively, against which the molar teeth are abutted vertically, and abutting portions abutted against side surfaces of the molar teeth when the molar teeth are abutted against the biting portions. Furthermore, the connecting rods of the mouthpiece are slightly longer than the tube, whereby each of the teeth grips is extracted to the outside of the tube.

BRIEF DESCRIPTION OF THE DRAWINGS

Objects, features and advantages other than those of the invention described above will sufficiently be understood in conjunction with the following description with reference to the accompanying drawings in which.

DETAILED DESCRIPTION OF THE PREFERRED EMBODIMENT

Figure 1:
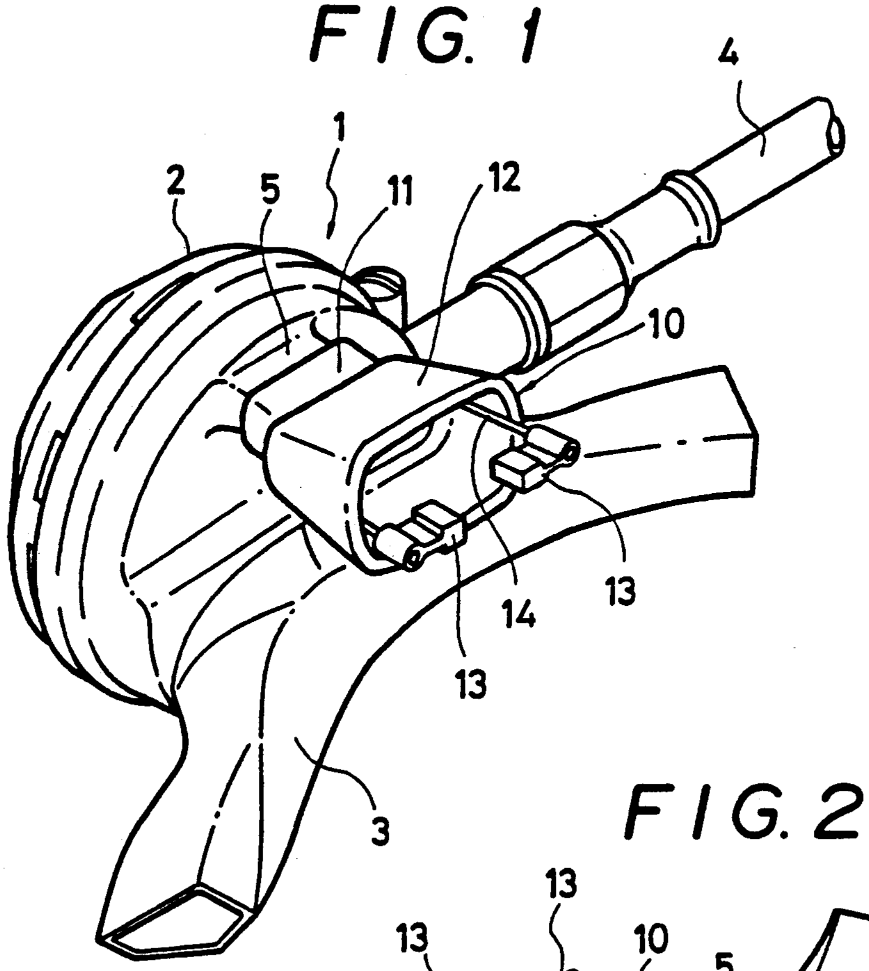
FIG. 1 is a perspective view showing a regulator to which an embodiment of the invention is applied.
Figure 2:
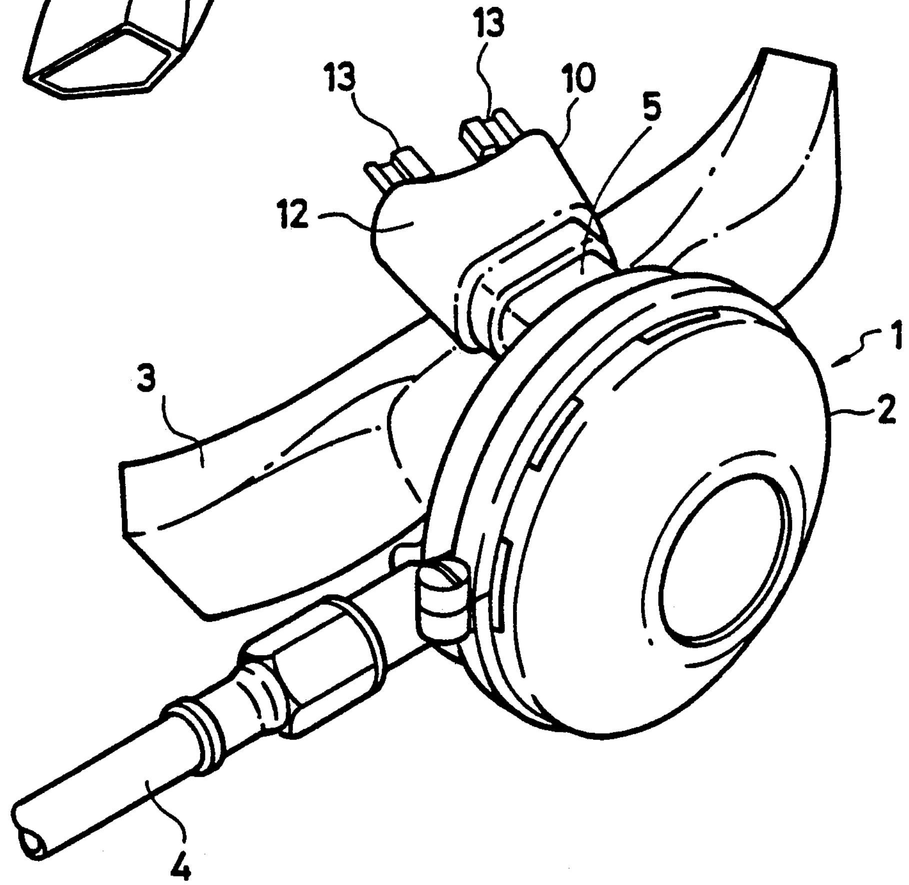
FIG. 2 is a perspective view showing the regulator to which the embodiment of the invention is applied, as viewed from a rear surface of the regulator.

FIGS. 1 and 2 show a regulator to which an embodiment of the invention is applied. The regulator 1 is arranged such that a mouthpiece 10 and an exhaust tube 3 are attached to a demand regulator unit 2. A hose 4 is connected to a side surface of the demand regulator unit 2. The hose 4 is connected to a bomb or cylinder (not shown) which is filled with compressed air. A valve and the like for reducing high pressure air supplied from the cylinder are incorporated into the demand regulator unit 2. An attaching tube 5 extends from a wearing side of the demand regulator unit 2. A mouthpiece 10 is mounted on the attaching tube 5. The exhaust tube 3 is so mounted on the demand regulator unit as to be located below the mouthpiece 10, to emit air exhausted from the mouthpiece 10 to the outside. Further, in order to prevent water from invading from the exhaust tube 3, the exhaust tube 3 is provided with a check valve (not shown) which executes closing operation only in an exhausting direction.

Figure 3:
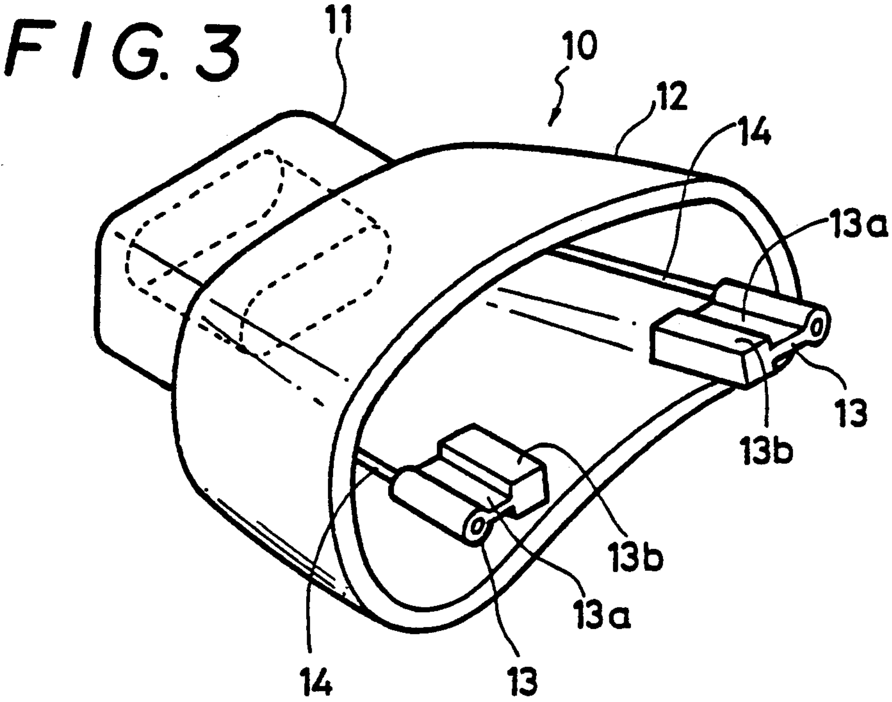
FIG. 3 is a perspective view showing a mouthpiece according to the embodiment of the invention.

FIG. 3 shows an entire arrangement of the mouthpiece 10. The mouthpiece 10 is provided with a connection 11 into which the attaching tube 5 of the demand regulator unit 2 is fitted detachably, and a tube 12 which is integrally connected to the connector 11 such that an interior of the tube 12 is in communication with the connector 11. The mouthpiece 10 is made of a soft elastic material such as plastic, rubber or the like as a whole. An end of the tube 12 opposite to the connection 11 is open, and air flows out from the open end. The tube 12 is arranged such that a portion thereof adjacent to the open end is substantially a horizontally elliptic configuration correspondingly to the mouth portion of the diver. Upon wearing of the regulator 1, the open end of the tube 12 is abutted against the outer side of the mouth of the diver A (refer to FIGS. 4 and 5).

Furthermore, the mouthpiece 10 is provided with a pair of teeth grips 13. The teeth grips 13 are integrally provided respectively with connecting rods 14 which are inserted into the tube 12 of the mouthpiece 10. Inserting ends of the respective connecting rods 14 are coupled to the tube 12, whereby the teeth grips 13 are integrated with the tube 12. The connecting rods 14 are slightly longer than the tube 12, whereby each of the teeth grips 13 is under such a condition as to be extracted to the outside of the tube 12. The teeth grips 13 arranged in this manner are located adjacent to molar teeth in a cavum oris B of the diver A, upon wearing of the teeth grips 13, whereby the teeth grips 13 are bitten and held by the molar teeth. In order to execute such biting and holding stably, the teeth grips 13 are integrally provided respectively with laminated biting portions 13*a* against which the molar teeth abut vertically, and abutting portion 13*b* which are abutted respectively against the side surfaces of the molar teeth when the molar teeth are abutted against the biting portions 13*a*.

Figure 4:
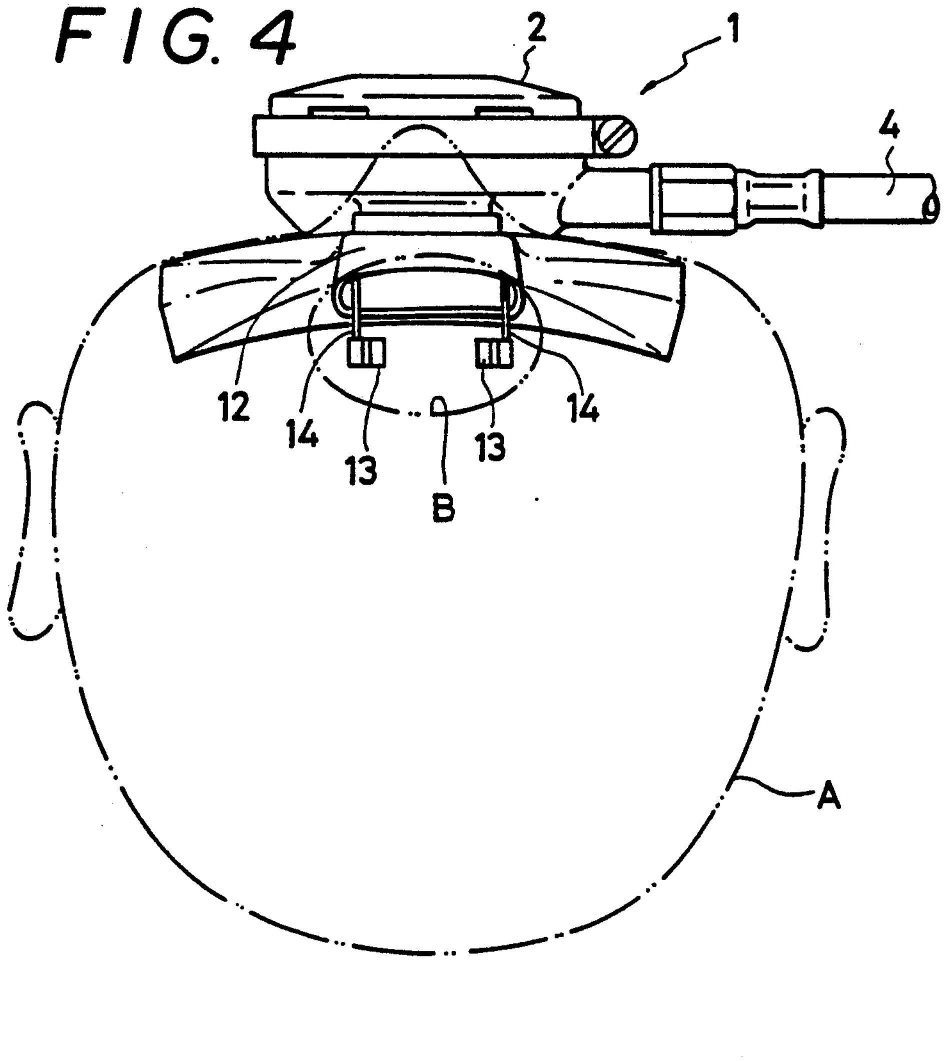
FIG. 4 is a top plan view showing a condition where the regulator is worn.
Figure 5:
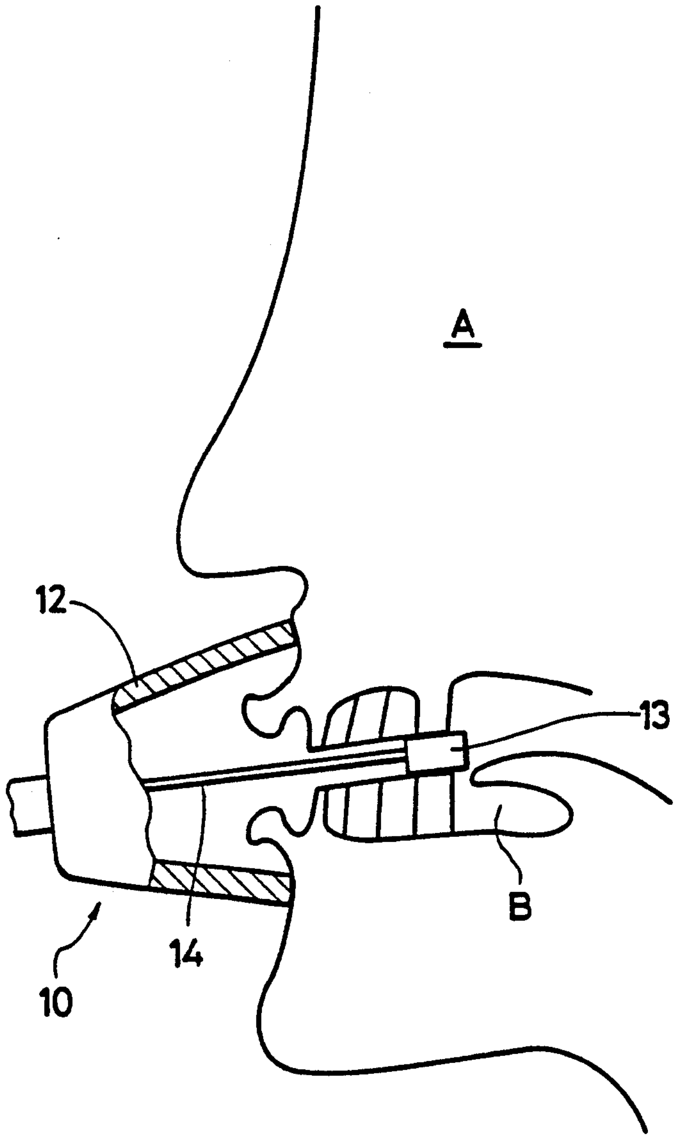
FIG. 5 is a side cross-sectional view showing the condition under which the regulator is worn.
Figure 6:
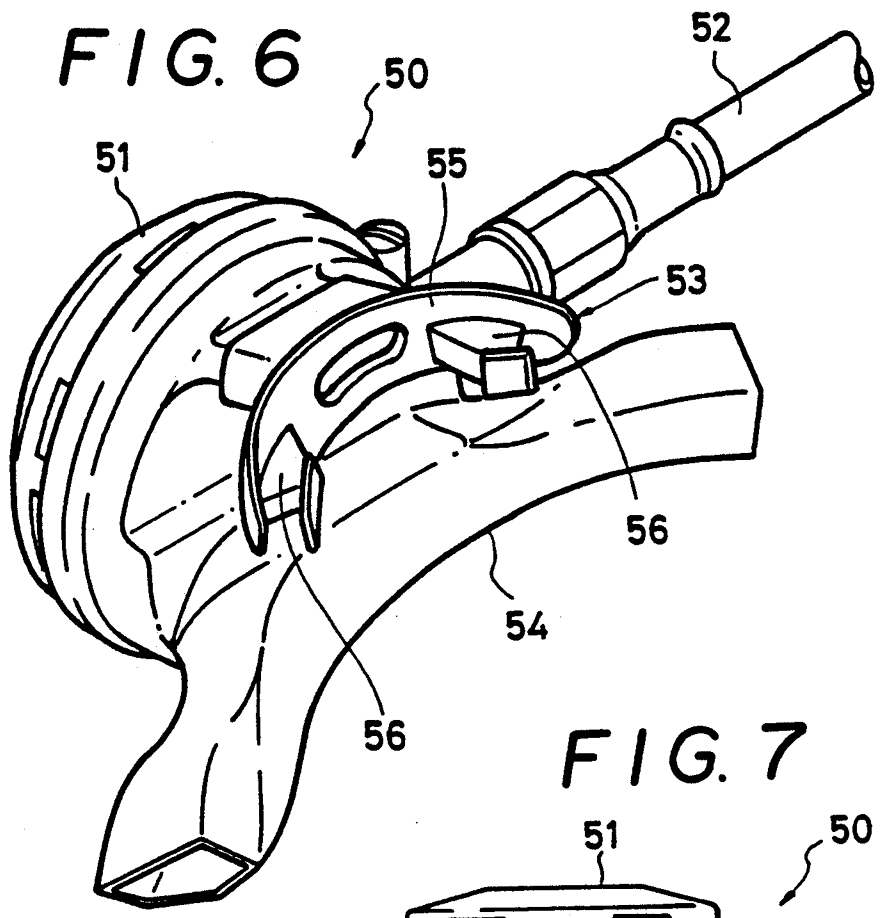
FIG. 6 is a perspective view showing a regulator which uses a conventional mouthpiece.
Figure 7:
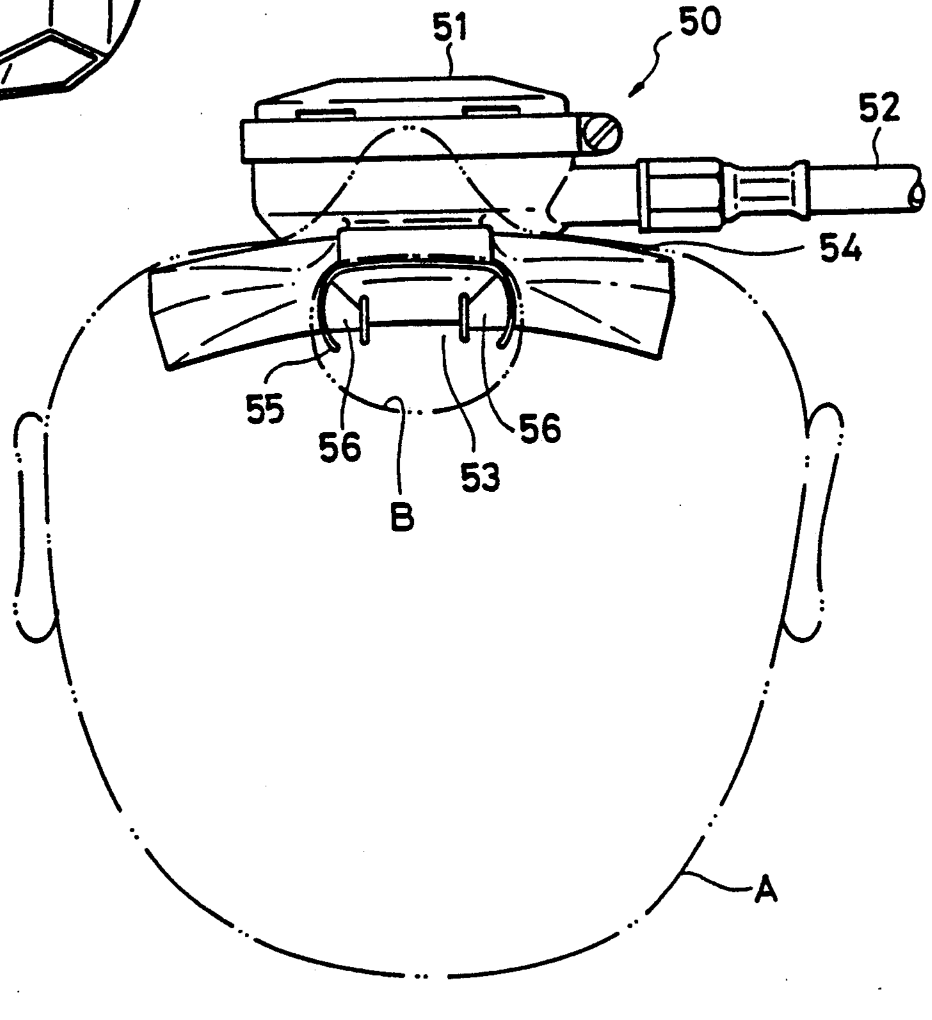
FIG. 7 is a top plan view showing a condition under which the regulator which uses the conventional mouthpiece is worn.
Figure 8:
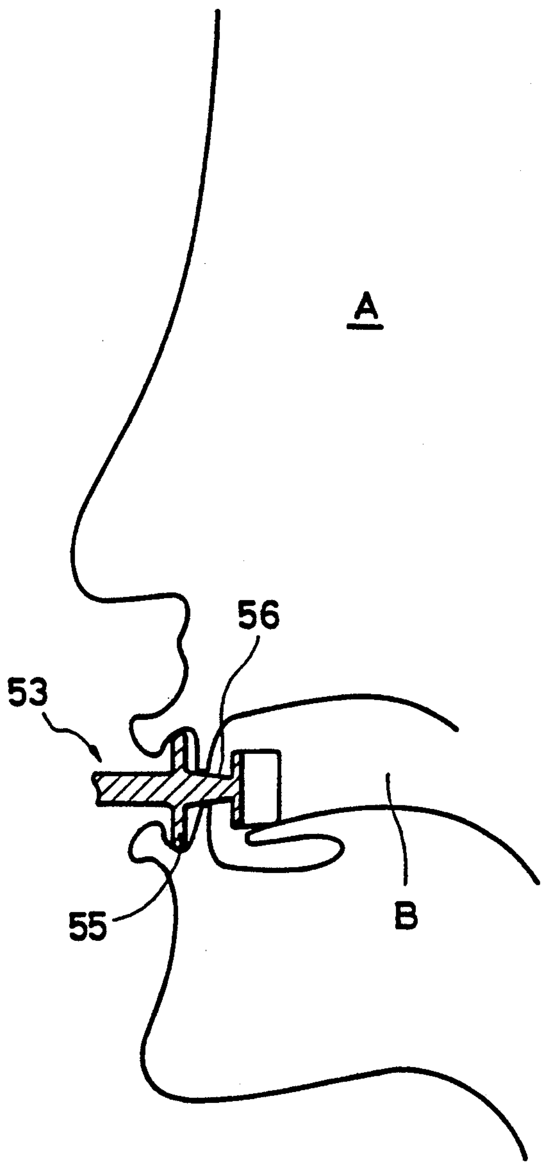
FIG. 8 is a side cross-sectional view showing a condition where the regulator which uses the conventional mouthpiece is worn.

FIGS. 4 and 5 show a wearing condition of the regulator 1 arranged as described above. The diver A positions the mouthpiece 10 such that the tube 12 is abutted against the outer side of the mouth, and the teeth grips 13 are inserted into the cavum oris B. Thus, the teeth grips 13 reach the molar teeth within the cavum oris B. Accordingly, the diver A bites and holds the teeth grips 13 by the molar teeth, whereby the regulator 1 is worn, and air is supplied into the cavum oris B.

The invention is arranged as described above. Accordingly, at wearing, the foreteeth do not bite and hold the teeth grips 13, dissimilarly to the conventional arrangement. The molar teeth bite and grip the teeth grips 13, and the tube 12 is abutted against the outer side of the mouth. Accordingly, the mouth portion is made relatively free, and it is possible to execute opening and closing of the mouth optionally. For this reason, also at wearing, the diver is free to utter words and talk as compared with the conventional regulator. Thus, it is possible to provide the regulator which is highly convenient in use.

The invention should not be limited to the embodiment described above, but many modifications are possible. For example, the arrangement may be such that the connecting rod of the mouthpiece 10 is brought to an addition or extension structure, to conform to the dimension or size of the cavum oris B of the driver A.

As described above, the invention is arranged such that the mouthpiece is formed by the tube abutted against the outer side of the mouth of the diver, and the teeth grips inserted toward the molar teeth of the mouth of the diver from the tube and bitten and held by the molar teeth. Accordingly, the degree of freedom of uttering words and talking even upon wearing of the mouthpiece increases by a simple structure. Thus, it becomes convenient in use. It is possible to provide a mouthpiece of this kind which does not exist conventionally.

What is claimed is:

1. A mouthpiece of a regulator, which is mounted on a demand regulator unit connected to a cylinder through a hose, to supply air from said cylinder into a cavum oris of a diver, the mouthpiece comprising:
   - a mouthpiece tube which abuts against an outer side of the cavum oris of the diver when the mouthpiece is worn by the diver, said tube being connected with and in communication with said demand regulator unit, and
   - a pair of teeth grips extending from said tube toward molar teeth in the cavum oris of the diver so as to be bitten and held by the molar teeth, said teeth grips being integrally provided with:
     - connecting rods, respectively, which are inserted into the tube of said mouthpiece, each said connecting rod having an inserting end coupled to said tube so as to be integral with said tube, said connecting rods being slightly longer than said tube such that each of said teeth grips is extracted to the outside of said tube,
     - laminate biting portions, respectively, against which the molar teeth are vertically abutted, said laminate biting portions being connected at free ends of said connecting rods,
     - abutting portions abutted against side surfaces of the molar teeth when the molar teeth are abutted against said biting portions, said abutting portions being connected at free ends of said connecting rods.

2. A mouthpiece of a regulator according to claim 1, wherein an exhaust tube through which air exhausted from the mouthpiece is emitted to the outside is mounted on said demand regulator unit so as to be located below the mouthpiece.

3. A mouthpiece of a regulator according to claim 1, further comprising a connection into which an attaching tube of the demand regulator unit is detachably inserted, and said mouthpiece tube being integrally connected to said connection such that an interior of said mouthpiece tube is in communication with said connection, said mouthpiece tube having a side wall adjacent to an open end thereof, said side wall substantially having the form of a horizontally elliptic configuration corresponding to a mouth portion of the diver, and said mouthpiece is made of a soft elastic material.

4. A mouthpiece of a regulator according to claim 1, wherein said soft elastic material is selected from the group consisting of plastic and rubber.

5. A mouthpiece of a regulator according to claim 1, wherein each said laminate biting portion abuts substantially only against one upper molar tooth and one corresponding lower molar tooth.

* * * * *